US008144192B2

(12) United States Patent
Matsui (10) Patent No.: US 8,144,192 B2
(45) Date of Patent: Mar. 27, 2012

(54) SIMPLIFIED IMAGE DISPLAY APPARATUS AND RECEIVING SYSTEM

(75) Inventor: Akira Matsui, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 1429 days.

(21) Appl. No.: 11/631,274

(22) PCT Filed: Feb. 8, 2006

(86) PCT No.: PCT/JP2006/302194
§ 371 (c)(1),
(2), (4) Date: Feb. 26, 2007

(87) PCT Pub. No.: WO2006/112112
PCT Pub. Date: Oct. 26, 2006

(65) Prior Publication Data
US 2008/0004494 A1    Jan. 3, 2008

(30) Foreign Application Priority Data

Apr. 14, 2005  (JP) .................................. 2005-117522

(51) Int. Cl.
*A61B 1/00* (2006.01)
*A61B 1/04* (2006.01)

(52) U.S. Cl. ............ 348/75; 348/65; 600/160; 600/117; 600/118

(58) Field of Classification Search .................... 348/75, 348/65; 600/160, 101, 117, 118, 424
See application file for complete search history.

(56) References Cited

U.S. PATENT DOCUMENTS

| 4,853,772 A | 8/1989 | Kikuchi |
| 7,069,057 B2 * | 6/2006 | Ishibashi et al. .............. 455/566 |
| 2004/0024288 A1 * | 2/2004 | Uchikubo ..................... 600/101 |
| 2004/0104999 A1 | 6/2004 | Okada |

(Continued)

FOREIGN PATENT DOCUMENTS

JP           63-318927           12/1988

(Continued)

OTHER PUBLICATIONS

Hasegawa et al., Capsule type endoscope apparatus, Jul. 28, 2005, Japan Patent Application Publication 2005-198789 (Application Number: 2004-007379).*

(Continued)

*Primary Examiner* — Wing Chan
*Assistant Examiner* — Ruolei Zong
(74) *Attorney, Agent, or Firm* — Scully, Scott, Murphy & Presser, P.C.

(57) ABSTRACT

To realize a simplified image display apparatus that prevents electrical connection between an external monitor and a receiving device when an electric signal generated by the receiving device is transmitted to the external monitor. The simplified image display apparatus includes a photocoupler 23 formed of a light emitting unit 21 electrically connected only to an input terminal 10 and a light receiving unit 22 that receives light output from the light emitting unit 21, a demodulator 24 that demodulates a received radio signal, a switching unit 25 that outputs either one of electric signals from the photocoupler 23 and from the demodulator 24, and a data generator 26 that applies predetermined signal processing to the electric signal input from the switching unit 25 to generate image data, and outputs the image data to a display unit 9 and an output terminal 11.

7 Claims, 7 Drawing Sheets

U.S. PATENT DOCUMENTS

| | | |
|---|---|---|
| 2004/0113498 A1 | 6/2004 | Kroenke |
| 2004/0249291 A1 | 12/2004 | Honda et al. |
| 2005/0038321 A1 | 2/2005 | Fujita et al. |
| 2005/0054902 A1* | 3/2005 | Konno .......................... 600/176 |
| 2005/0119582 A1* | 6/2005 | Matsumura et al. .......... 600/509 |
| 2005/0124858 A1 | 6/2005 | Matsuzawa et al. |

FOREIGN PATENT DOCUMENTS

| | | |
|---|---|---|
| JP | 2003-19111 | 1/2003 |
| JP | 2003-235795 | 8/2003 |
| JP | 2004-159833 | 6/2004 |
| JP | 2005-74034 | 3/2005 |
| JP | 2005-80713 | 3/2005 |
| JP | 2005-80789 | 3/2005 |
| WO | WO 2005/031650 A1 | 4/2005 |

OTHER PUBLICATIONS

Extended Supplementary European Search Report dated Oct. 15, 2009.

Japanese Office Action dated Mar. 1, 2011 issued in JP 2005-117522, together with English translation.

* cited by examiner

SIMPLIFIED IMAGE DISPLAY APPARATUS AND RECEIVING SYSTEM

TECHNICAL FIELD

The present invention relates to a simplified image display apparatus that generates image data based on an electric signal generated by a receiving device that receives a predetermined radio signal in a state of being carried by a subject, and can display an image based on the generated image data and can output the image data to an external device, and a receiving system including the simplified image display apparatus.

BACKGROUND ART

Recently, in the field of endoscope, a swallowable capsule endoscope has been proposed. This capsule endoscope is provided with an imaging function and a radio communication function. The capsule endoscope has a function of moving in a body cavity, for example, inside of a stomach and a small intestine with peristalsis, after it is swallowed from the mouth of a subject for observation (examination) until it is naturally discharged, and imaging intra-subject images, for example, at intervals of 0.5 second.

While the endoscope is moving in the body cavity, image data imaged in the body by the capsule endoscope is sequentially transmitted to the outside by radio communications, and stored in a memory provided in a receiving device. If the subject carries the receiving device having the radio communication function and the memory function, the subject swallows the capsule endoscope and then can freely move until the endoscope is discharged (for example, see Patent Document 1).

In the above capsule endoscope system, after a series of imaging operation by the capsule endoscope are completed, the image data stored in the receiving device is generally transferred to a workstation or the like, and the images are viewed afterwards. However, there are strong demands from doctors for real-time viewing of the images of concerned spots or the like. There has been proposed a system including a simplified image display apparatus that displays images on a real-time basis based on the radio signal transmitted from the capsule endoscope.

The conventional simplified image display apparatus, in its simplest configuration, is configured to be electrically connectable to the receiving device, and includes a small display screen and a predetermined signal processing unit. By having such a configuration, the simplified image display apparatus can receive a signal having subjected to receiving processing by the receiving device, and display images imaged by the capsule endoscope on the small display screen based on the input signal after having performed predetermined processing.

Among the conventional simplified image display apparatuses, one having an output terminal for outputting the image data generated based on the signal input by the receiving device to an external monitor has been proposed. The configuration with the output terminal allows for, on the one hand, viewing of the image data on the small screen equipped on the simplified image display apparatus at a normal occasion, and on the other hand, display of the image on a large monitor of a TV receiver, for example, when a image displayed on the small screen suggests a presence of a lesion and more detailed examination is required.

Patent Document 1: Japanese Patent Application Laid-open No. 2003-19111

DISCLOSURE OF INVENTION

Problem to be Solved by the Invention

However, in the conventional simplified image display apparatus including the output terminal for the external monitor, the large monitor and the receiving device are electrically connected to each other, and hence the current flowing in the large monitor may reach the receiving device, thereby adversely affecting the subject carrying the receiving device.

In the conventional image display apparatus, the receiving device is used in a state of being carried by the subject (patient) constantly. Therefore, if large current is generated in the external monitor, for example, the large current can flow to the receiving device via the simplified image display apparatus. Particularly, since the external monitor that displays images on a large display screen has generally such a configuration that driving power is supplied from a home power source, a configuration for preventing the current from flowing from the external monitor to the receiving device via the simplified image display apparatus is required for the simplified image display apparatus.

The present invention has been achieved in order to solve the above problems. It is an object of the present invention to realize a simplified image display apparatus in which occurrence of electrical connection between the external monitor and the receiving device is prevented, and a receiving system including the simplified image display apparatus, in the simplified image display apparatus capable of displaying image data generated based on the electric signal output from the receiving device, which is used in a state of being carried by the subject, and capable of outputting the image data to the external monitor.

Means for Solving Problem

A simplified image display apparatus according to one aspect of the present invention is capable of generating image data based on an electric signal generated by receiving processing of a receiving device, which is used in a state of being carried by a subject, displaying images based on the generated image data, and outputting the image data to an external device, and includes: a non-linear output unit electrically connected to the receiving device at the time of use, to output the electric signal input from the receiving device non-linearly to an output target not using a conducting wire; a non-linear input unit electrically insulated from the non-linear output unit, to input the electric signal output from the non-linear output unit; a display unit that displays image data based on the electric signal input by the non-linear input unit; and an output terminal electrically connected to the external device, to output the image data based on the electric signal input by the non-linear input unit to the external device.

In the simplified image display apparatus, the electric signal input from the receiving device may be transmitted through the non-linear output unit not using the conducting wire and through the non-linear input unit. Accordingly, the receiving device and the external device are prevented from being electrically connected to each other when the electric signal generated by the receiving device is output to the external device, and it is avoided that leakage current from the external device flows into the receiving device.

In the simplified image display apparatus, the non-linear output unit may convert the electric signal input from the receiving device to an optical signal and outputs the optical signal, and the non-linear input unit may receive the optical signal output from the non-linear output unit, and apply photoelectric conversion processing to the received optical signal, thereby reproducing the electric signal.

In the simplified image display apparatus, the non-linear output unit and the non-linear input unit may form a photocoupler.

In the simplified image display apparatus, the non-linear output unit may transmit a radio signal generated based on the electric signal, and the non-linear input unit may receive the radio signal, and apply predetermined receiving processing to the radio signal, thereby reproducing the electric signal.

In the simplified image display apparatus, the non-linear output unit and the non-linear input unit may be formed in a transmission unit formed detachably relative to a simplified image display apparatus main body, and the output terminal may be electrically connected to the non-linear input unit only when the transmission unit is attached to the simplified image display apparatus main body.

In the simplified image display apparatus, the output terminal may be electrically connected to a first terminal arranged on a surface of the transmission unit and on a face brought into contact with the simplified image display apparatus main body at the time of attachment, and the non-linear input unit may be electrically connected to a second terminal arranged on a surface of the simplified image display apparatus main body and at a position brought into contact with the first terminal at the time of attachment of the transmission unit.

The simplified image display apparatus may further include an attachment detector that detects presence of attachment of a casing relative to the simplified image display apparatus main body, and a conduction controller that controls electrical conduction between the non-linear input unit and the non-linear output unit based on a detection result of the attachment detector.

A receiving system according to another aspect of the present invention includes a receiving device carried by a subject to perform receiving processing of a radio signal transmitted from a body-insertable apparatus inserted into the subject, and a simplified image display apparatus capable of generating image data based on an electric signal acquired by receiving processing of the receiving device, displaying images based on the generated image data, and outputting the image data to an external device, wherein the receiving device includes a demodulator that performs demodulation of the radio signal received via a predetermined receiving antenna, and an output terminal that outputs at least an electric signal demodulated by the demodulator to the outside, and the simplified image display apparatus includes an input terminal electrically connected to the output terminal at the time of use to input the electric signal, a non-linear output unit that non-linearly outputs the electric signal input from the receiving device via the input terminal to an output target not using a conducting wire, a non-linear input unit electrically insulated from the non-linear output unit, to input the electric signal output from the non-linear output unit, a display unit that displays image data based on the electric signal input by the non-linear input unit, and an output terminal electrically connected to the external device, to output the image data based on the electric signal input by the non-linear input unit to the external device.

Effect Of The Invention

The simplified image display device and the receiving system according to the present invention have such a configuration that the electric signal input from the receiving device is transmitted via the non-linear output unit not using the conducting wire and the non-linear input unit. Accordingly, the receiving device and the external device are prevented from being electrically connected to each other when the electric signal generated by the receiving device is output to the external device, and it is avoided that the leakage current from the external device flows into the receiving device.

EXPLANATIONS OF LETTERS OR NUMERALS

1 Receiving system
2 Subject
3 Capsule endoscope
4 Receiving device
5 Simplified image display apparatus
6 External monitor
7a to 7h Receiving antenna
9 Display unit
10 Input terminal
11 Output terminal
12 Input unit
13 Receiving antenna
14 Antenna selector
15 Demodulator
16 Data generator
17 Recording unit
18 Output terminal
19 Power supply unit
21 Light emitting unit
22 Light receiving unit
23 Photocoupler
24 Demodulator
25 Switching unit
26 Data generator
27 Driving controller
28 Power supply unit
29 Receiving device
30 Simplified image display apparatus
31 Simplified image display apparatus
32 Radio transmitting unit
33 Radio receiving unit
34 Transmitting unit
35 Simplified image display apparatus main body
38 Simplified image display apparatus
39 Simplified image display apparatus main body
40 Transmission unit
41 to 44 Terminal 45 Simplified image display apparatus
46 Simplified image display apparatus main body
47 Transmission unit
48 Connection detector
49 Switching unit
50 Conduction controller
51 Switching element

BEST MODE(S) FOR CARRYING OUT THE INVENTION

A simplified image display apparatus and a receiving system including the simplified image display apparatus according to best modes for carrying out the invention (hereinafter, simply "embodiment") will be explained below. Note that the drawings are schematic, and that a relationship between a thickness and a width of each part, and a rate of a thickness of each part are different from actual ones.

First Embodiment

A receiving system according to a first embodiment is explained first. A use mode of the receiving system according to the first embodiment is explained first, and a configuration, operation, and the like of the receiving system are explained next.

Figure 1:
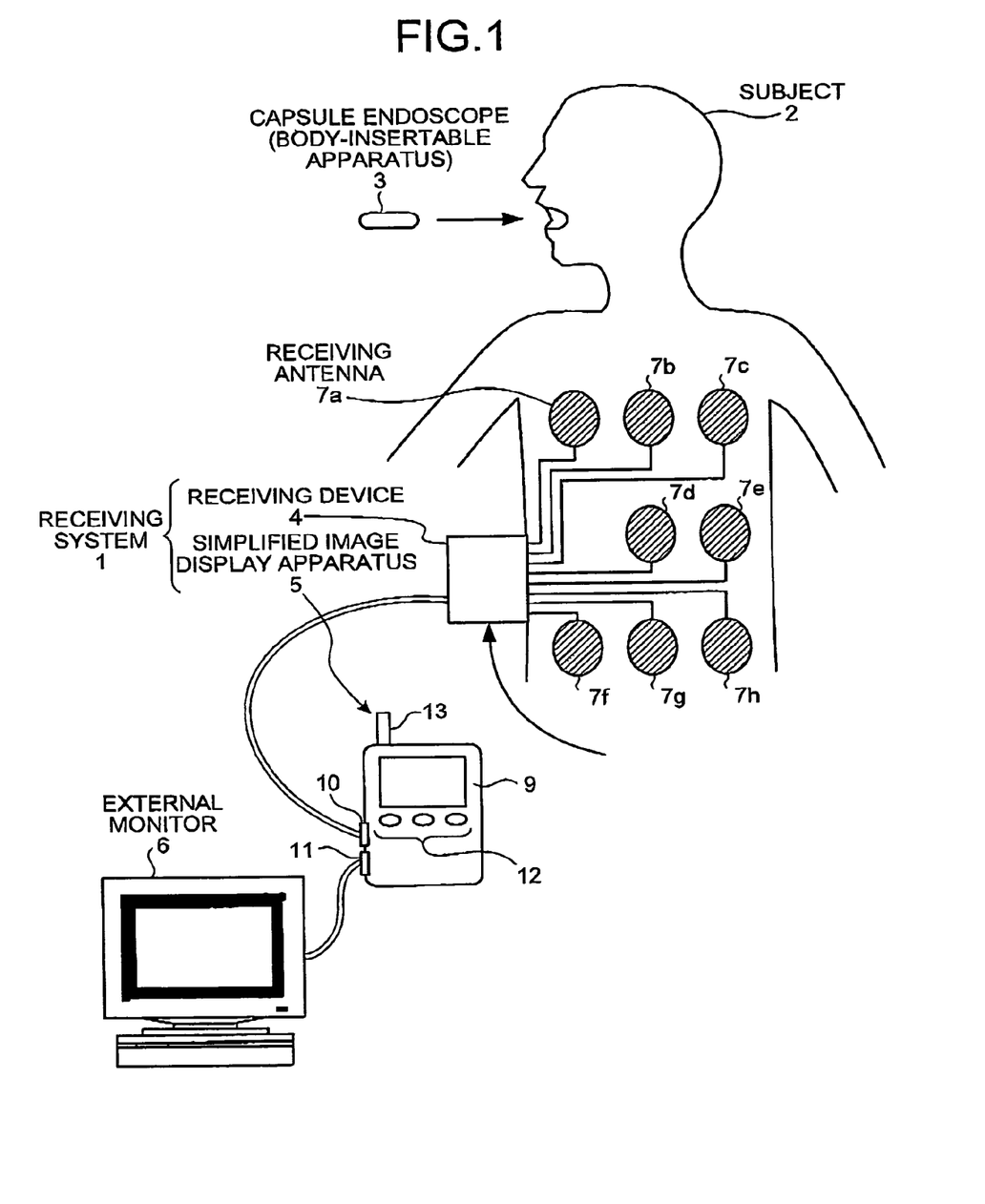
FIG. 1 is a schematic diagram of a use mode of a receiving system.

FIG. 1 is a schematic diagram of the use mode of the receiving system according to the first embodiment. As shown in FIG. 1, a receiving system 1 according to the first embodiment is used for receiving processing of a radio signal transmitted from a capsule endoscope 3 inserted into a subject 2. Specifically, the receiving system 1 according to the first embodiment includes a receiving device 4 used in a state of being carried by the subject 2 to receive a radio signal received via antennas 7a to 7h, and a simplified image display apparatus 5 connected to the receiving device 4 to display an image taken by the capsule endoscope 3 based on the electric signal output from the receiving device 4, and output data to an external monitor 6.

The capsule endoscope 3 functions as an example of a body-insertable apparatus. Specifically, the capsule endoscope 3 is inserted into the subject 2 from the mouth of the subject 2 and has a function for performing radio transmission of the image data acquired by, for example, a built-in imaging mechanism to the outside of the subject 2.

The external monitor 6 functions as an example of an external device, and is used at the time of detailed observation of the image taken by the capsule endoscope 3. In other words, the simplified image display apparatus 5 constituting the receiving system 1 according to the first embodiment also has an image display function, however, since the simplified image display apparatus 5 is formed in a small size, taking portability into consideration, it is required that the external monitor 6 is used when there is a possibility of occurrence of a lesion and more detailed observation is required. As a specific configuration of the external monitor 6, a general monitor device including a screen having a predetermined display area, and capable of inputting image data from the outside can be used, and in the first embodiment, a TV receiver driven by a home power source is used as the external monitor 6.

The receiving device 4 receives the radio signal transmitted from the capsule endoscope 3 via the receiving antennas 7a to 7h, to perform the predetermined receiving processing. As shown in FIG. 1, the receiving device 4 is used in a state of being carried by the subject 2. By using the receiving device 4 in this manner, the subject 2 can freely move, with the capsule endoscope 3 being inserted in the body. In the example of FIG. 1, the receiving device 4 and the simplified image display apparatus 5 are connected with each other via a predetermined cable. However, the receiving device 4 and the simplified image display apparatus 5 are not always used in the state of being connected with each other, and in a normal state in which real time observation of the image in the subject is not performed, the subject 2 carries only the receiving device 4, thereby being allowed free movement.

The simplified image display apparatus 5 has a function for displaying an image based on an electric signal output from the receiving device 4 and outputting the image data to the external monitor 6. To realize such a function, the simplified image display apparatus 5 includes, as shown in FIG. 1, a display unit 9 that displays images, an input terminal 10 for electrically connecting to the receiving device 4, an output terminal 11 for electrically connecting to the external monitor 6, and an input unit 12 that performs control of driving state and the like. The simplified image display apparatus 5 generally has a configuration capable of directly receiving the radio signal transmitted from the capsule endoscope 3, not using the receiving device 4, and the simplified image display apparatus 5 according to the first embodiment includes a receiving antenna 13 for realizing the receiving function.

Figure 2:
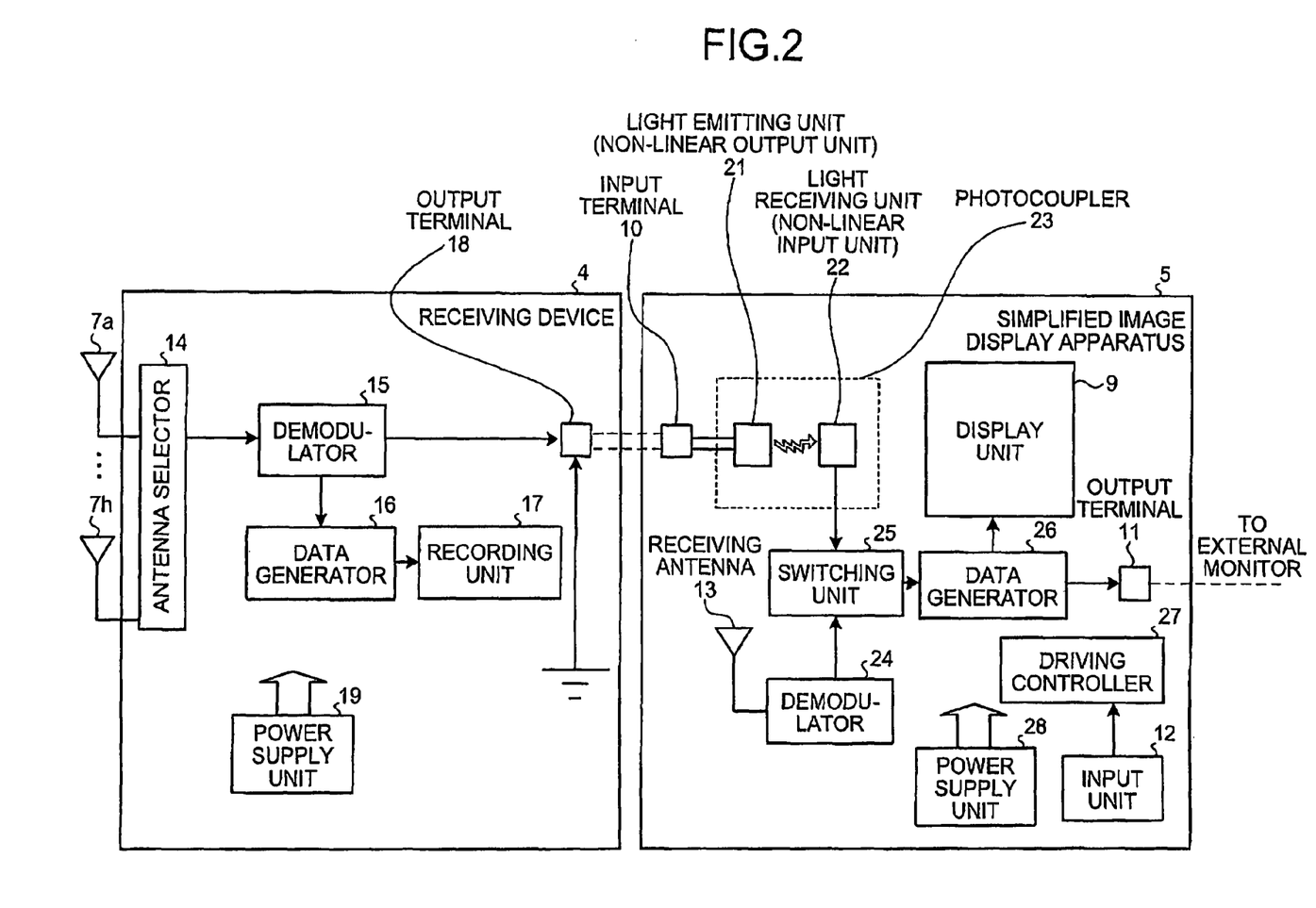
FIG. 2 is a schematic block diagram showing a configuration of a receiving system according to a first embodiment.

The configuration of the receiving device 4 and the simplified image display apparatus 5 is explained next in detail. FIG. 2 is a schematic block diagram showing the configuration of the receiving device 4 and the simplified image display apparatus 5 constituting the receiving system according to the first embodiment. As shown in FIG. 2, the receiving device 4 includes an antenna selector 14 that selects one of the receiving antennas 7a to 7h, a demodulator 15 that demodulates the radio signal received via the receiving antenna selected by the antenna selector 14, a data generator 16 that generates image data corresponding to the image acquired by the capsule endoscope 3 based on the demodulated electric signal, and a recording unit 17 that records the image data generated by the data generator 16. The receiving device 4 includes an output terminal 18 for outputting the electric signal demodulated by the demodulator 15 to the simplified image display apparatus 5, and a power supply unit 19 that supplies driving power to the respective components.

The antenna selector 14 selects the receiving antenna suitable for receiving the radio signal transmitted from the capsule endoscope 3 from the receiving antennas 7a to 7h. As a specific selection mechanism of the antenna selector 14, for example, the antenna selector 14 compares strength of the radio signals received by respective receiving antennas 7a to 7h, to select a receiving antenna having the highest strength of the radio signal.

The recording unit 17 has a function for recording the image data generated by the data generator 16 used for viewing afterwards in a workstation and the like. As a specific configuration of the recording unit 17, a predetermined memory, a hard disk, or the like can be built in. However, in the first embodiment, the recording unit 17 has a function for recoding the image data in a Compact Flash (registered trademark) memory.

The output terminal 18 outputs the electric signal demodulated by the demodulator 15 to the simplified image display apparatus 5. Specifically, the output terminal 18 is formed such that it can be electrically connected to the input terminal 10 included in the simplified image display apparatus 5 via the predetermined cable or the like, thereby outputting the electric signal to the simplified image display apparatus 5 via the cable or the like. Further, the output terminal 18 has a configuration of receiving supply of a power source and an earth potential, so that when the cable or the like connecting the output terminal 18 and the input terminal 10 with each other is formed of, for example, a coaxial cable, the output terminal 18 outputs not only the electric signal from the demodulator 15 but also the power source and the earth potential to the simplified image display apparatus 5.

The configuration of the simplified image display apparatus 5 is explained in detail. The simplified image display apparatus 5 includes a photocoupler 23 formed of a light emitting unit (a non-linear output unit) 21 electrically connected only to the input terminal 10 and a light receiving unit (a non-linear input unit) 22 that receives light output from the light emitting unit 21, a demodulator 24 that demodulates the radio signal received via the receiving antenna 13, a switching unit 25 that inputs the electric signals from the photocoupler 23 and the demodulator 24 to output either one of the electric signals, and a data generator 26 that applies predetermined signal processing to the electric signal input from the switching unit 25 to generate image data, and outputs the image data to the display unit 9 and the output terminal 11. The simplified image display apparatus 5 also includes a driving controller 27 that performs a predetermined control based on the content input via the input unit 12 and a power supply unit 28 that supplies driving power to the respective components other than the light emitting unit 21.

The input terminal 10 inputs the electric signal acquired by the receiving device 4 based on the received radio signal. Specifically, the input terminal 10 is electrically connected to the output terminal 18 equipped in the receiving device 4 via a coaxial cable or the like. The electric signal demodulated by the demodulator 15, the power source, and the earth potential are supplied to the input terminal 10.

The light emitting unit 21, which is one component of the photocoupler 23, functions as an example of the non-linear output unit. Specifically, the light emitting unit 21 has a function for outputting an optical signal corresponding to the input electric signal. Therefore, the light emitting unit 21 can perform non-linear output to the output target, not using a conducting wire. Specifically, the light emitting unit 21 realizes the non-linear output by not outputting the electric signal by the conducting wire, but outputting an optical signal corresponding to the electric signal. To realize such a function, the light emitting unit 21 has a configuration including a light emitting element, for example, a light emitting diode of a semiconductor laser element, and a necessary drive circuit. The light emitting unit 21 is arranged in a state of electrically insulated from the components other than the input terminal 10, and is driven based on the electric signal, the power source, and the earth potential supplied from the receiving device 4 side via the input terminal 10.

The light receiving unit 22, which is the other component of the photocoupler 23, functions as an example of the non-linear input unit. Specifically, the light receiving unit 22 is arranged in a state of electrically insulated from the light emitting unit 21, and has a function for receiving the optical signal output from the light emitting unit 21 to reproduce the received optical signal to the electric signal by performing photoelectric conversion processing. As a specific component of the light receiving unit 22, the light receiving unit 22 is formed of, for example, a photodiode, a phototransistor, or the like having a photoelectric conversion function.

The demodulator 24 demodulates the radio signal received via the receiving antenna 13 equipped in the simplified image display apparatus 5. The simplified image display apparatus 5 according to the first embodiment not only performs display of the image, upon reception of the electric signal from the receiving device 4, but also can independently display an image by receiving the radio signal from the capsule endoscope 3. The simplified image display apparatus 5 includes the receiving antenna 13 and the demodulator 24 therein corresponding to such a function. As a specific configuration of the demodulator 24, the demodulator can be the same as the demodulator 15 equipped in the receiving device 4.

The switching unit 25 is electrically connected to the light receiving unit 22 and the demodulator 24 to switch the electric signal to be output to the data generator 26, of the electric signals input from the light receiving unit 22 and the demodulator 24. Switching of the electric signal to be output is performed by the control of the driving controller 27 based on an instruction from a user input via the input unit 12.

The data generator 26 generates the image data based on the electric signal output from the switching unit 25. The image data generated by the data generator 26 is output to the display unit 9 and the output terminal 11. Since image display is performed on the external monitor 6 based on the image data generated by the data generator 26, a general format is preferably used as the format of the image data generated by the data generator 26.

The display unit 9 simply displays the image of the inside of the subject acquired by the capsule endoscope 3. The display unit 9 is formed of a small screen such as a liquid crystal display or the like, and the user can ascertain an outline of the image in the subject on a real time basis by viewing the display unit 9.

The output terminal 11 has a function for outputting the image data generated by the data generator 26 to the external monitor 6 by electrically connecting the output terminal 11 to the external monitor 6. The output terminal 11 and the external monitor 6 are electrically connected via the predetermined cable or the like as shown in FIG. 1.

An operation of the receiving system according to the first embodiment is explained next. Among the operations of the receiving system, an instance in which the receiving device 4 receives the radio signal transmitted from the capsule endoscope 3, and the receiving system transmits the image data based on the signal received by the receiving device 4 to the external monitor 6 to display an image on the screen of the external monitor 6 is explained.

The radio signal transmitted from the capsule endoscope 3 via the receiving antenna 7 selected by the antenna selector 14 equipped in the receiving device 4 is received. The received radio signal is demodulated by the demodulator 15, and the demodulated electric signal and the earth potential generated in the receiving device 4 are output to the input terminal 10 equipped in the simplified image display apparatus 5 via the output terminal 18 and the coaxial cable connected to the output terminal 18.

The light emitting unit 21 is then driven by a power-supply voltage supplied via the input terminal 10, and the electric signal is converted to an optical signal by emitting light having brightness corresponding to the potential difference between the earth potential supplied via the input terminal and the electric signal, and is output. The output optical signal is received by the light receiving unit 22 electrically insulated from the light emitting unit 21, and the light receiving unit 22 applies photoelectric conversion processing to the received optical signal, thereby reproducing the electric signal and output to the switching unit 25.

Thereafter, the electric signal reproduced by the light receiving unit 22 is input to the data generator 26 via the switching unit 25. The data generator 26 generates the image data in the general format based on the input electric signal, and outputs the image data to the external monitor 6 via the output terminal 11. Since the external monitor 6 displays the input image data on the screen, the image in the subject 2 acquired by the capsule endoscope 3 is displayed on the real time basis, thereby enabling detailed observation of the image by a doctor and the like.

An advantage of the receiving system according to the first embodiment is explained next. In the simplified image display apparatus 5 equipped in the receiving system according to the first embodiment, the external monitor 6 can perform image display based on the radio signal received by the receiving device 4, while maintaining the state in which the receiving device 4 and the external monitor 6 are electrically insulated from each other. That is, in the simplified image display apparatus 5, since the non-linear output unit (the light emitting unit 21) has a function for outputting the electric signal, not using the conducting wire, to the non-linear input unit (the light receiving unit 22), which is the output target, electrical connection between the non-linear output unit and the non-linear input unit is disconnected, and hence the receiving device 4 electrically connected to the non-linear output unit and the external monitor 6 electrically connected to the non-linear input unit are electrically insulated from each other. Therefore, for example, when short-circuit or the like occurs in the circuit structure of the external monitor 6, the large current does not flow into the receiving device 4, and hence it can be prevented that the subject 2 carrying the receiving device 4 is affected by the large current.

Further, in the first embodiment, since the configuration is such that the light emitting unit 21 is adopted as the non-linear output unit, and the light receiving unit 22 is adopted as the non-linear input unit, there is an advantage in that reliable signal transmission can be performed at low power consumption. In other words, the information transmission technology itself using the optical signal has been already established in the field of optical communication and the like, and by using the established technology, highly reliable signal transmission can be easily realized. Further, when the light emitting unit 21 is formed of a light emitting diode, since the driving power of the light emitting diode can be set to a quite small value, there is another advantage in that the power consumption can be reduced. In the first embodiment, both of the light emitting unit 21 and the light receiving unit 22 are built in the simplified image display apparatus, and when these units are arranged adjacent to each other, the optical signal output from the light emitting unit 21 can be made a small value. As a result, there is another advantage in that the power consumption can be further reduced, as compared to the case of optical communication.

Modified Example

Figure 3:
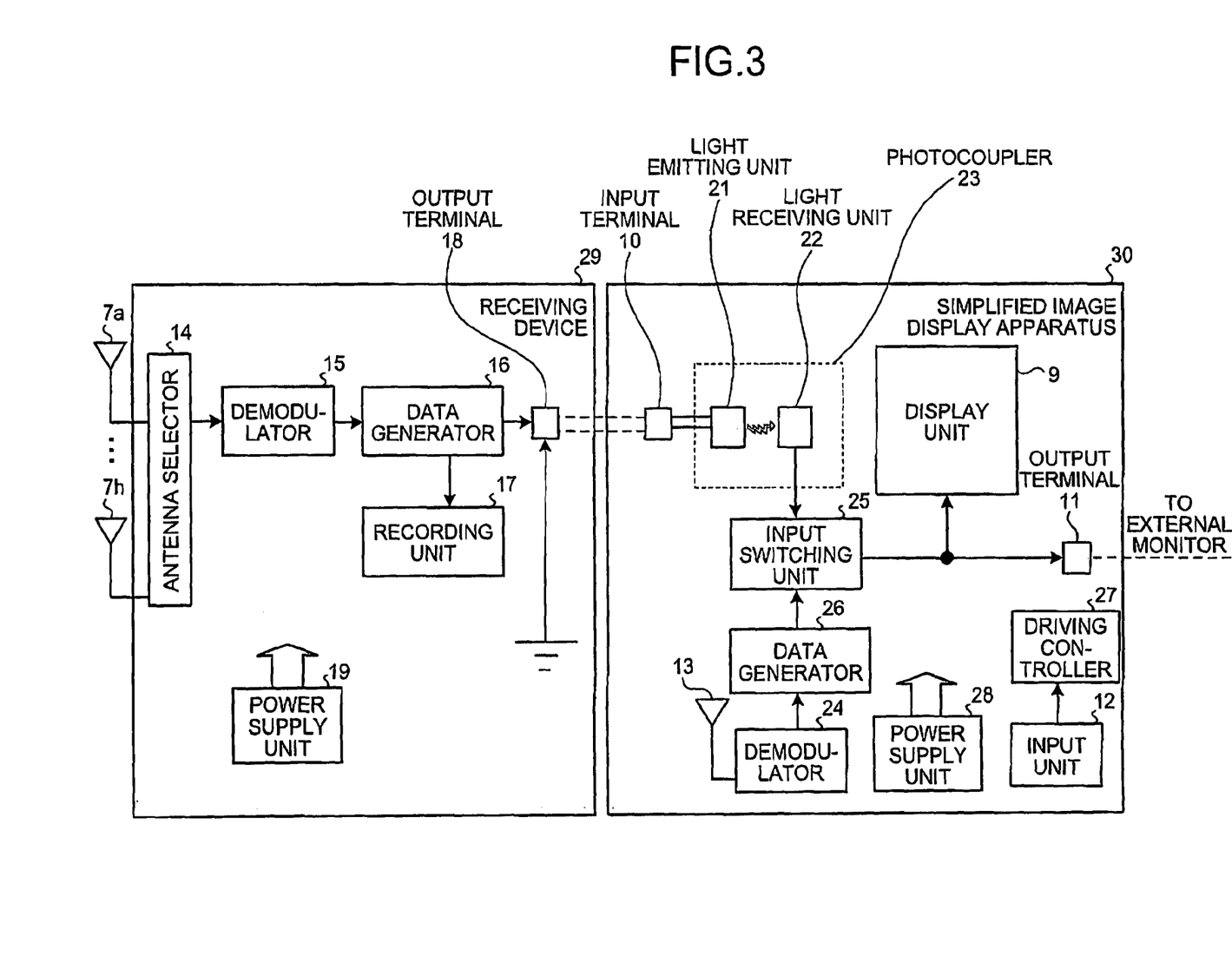
FIG. 3 is a schematic block diagram showing a configuration of a receiving system according to a modified example of the first embodiment.

A modified example of the receiving system according to the first embodiment is explained next. The receiving system according to the modified example does not use the demodulated electric signal as in the first embodiment, as the electric signal to be output from the receiving device, but outputs image data generated by the data generator 16.

FIG. 3 is a schematic block diagram showing a configuration of the receiving system according to the modified example. In the receiving system according to the modified example, the demodulator 15 and the output terminal 18 are not directly connected to each other inside a receiving device 29, but the data generator 16 is arranged therebetween. As a result of adopting such a configuration, the electric signal output to a simplified image display apparatus 30 via the output terminal 18 is not the one demodulated by the demodulator 15, but the one generated by the data generator 16 as the image data.

A different configuration is adopted corresponding to a difference of the electric signal to be output, for the simplified image display apparatus 30. Specifically, the data generator 26, which is a component of the simplified image display apparatus 30, is not arranged between the switching unit 25 and the output terminal 11, but arranged between the demodulator 24 and the switching unit 25, and the switching unit 25 is directly connected to the display unit 9 and the output terminal 11, not using the data generator 26. This is because the electric signal reproduced by the light receiving unit 22 is in an image data format corresponding to that the electric signal output from the receiving device 29 becomes the image data. Therefore, to change the electric signal input from the receiving antenna 13 equipped in the simplified image display apparatus 30 to the switching unit 25 into the image data format, a configuration in which the data generator 26 is arranged between the demodulator 24 and the switching unit 25 is adopted in the modified example. Since the electric signal output from the switching unit 25 is in the image data format, the data generator 26 need not be arranged between the switching unit 25 and the display unit 9, and between the switching unit 25 and the output terminal 11, and hence the switching unit 25, the display unit 9, and the output terminal 11 are directly connected.

As the type of the electric signal output from the receiving device to the simplified image display apparatus, a signal in any format or a signal at any processing stage can be used, so long as it corresponds to the radio signal transmitted from the capsule endoscope 3. An electric signal in any format can enjoy the advantages explained in the first embodiment, since a pair of the non-linear output unit and the non-linear input unit is formed in the simplified image display apparatus.

Second Embodiment

The receiving system according to a second embodiment is explained next. In the receiving system according to the second embodiment, a configuration in which information is transmitted between the non-linear output unit and the non-linear input unit by radio communications is adopted.

Figure 4:
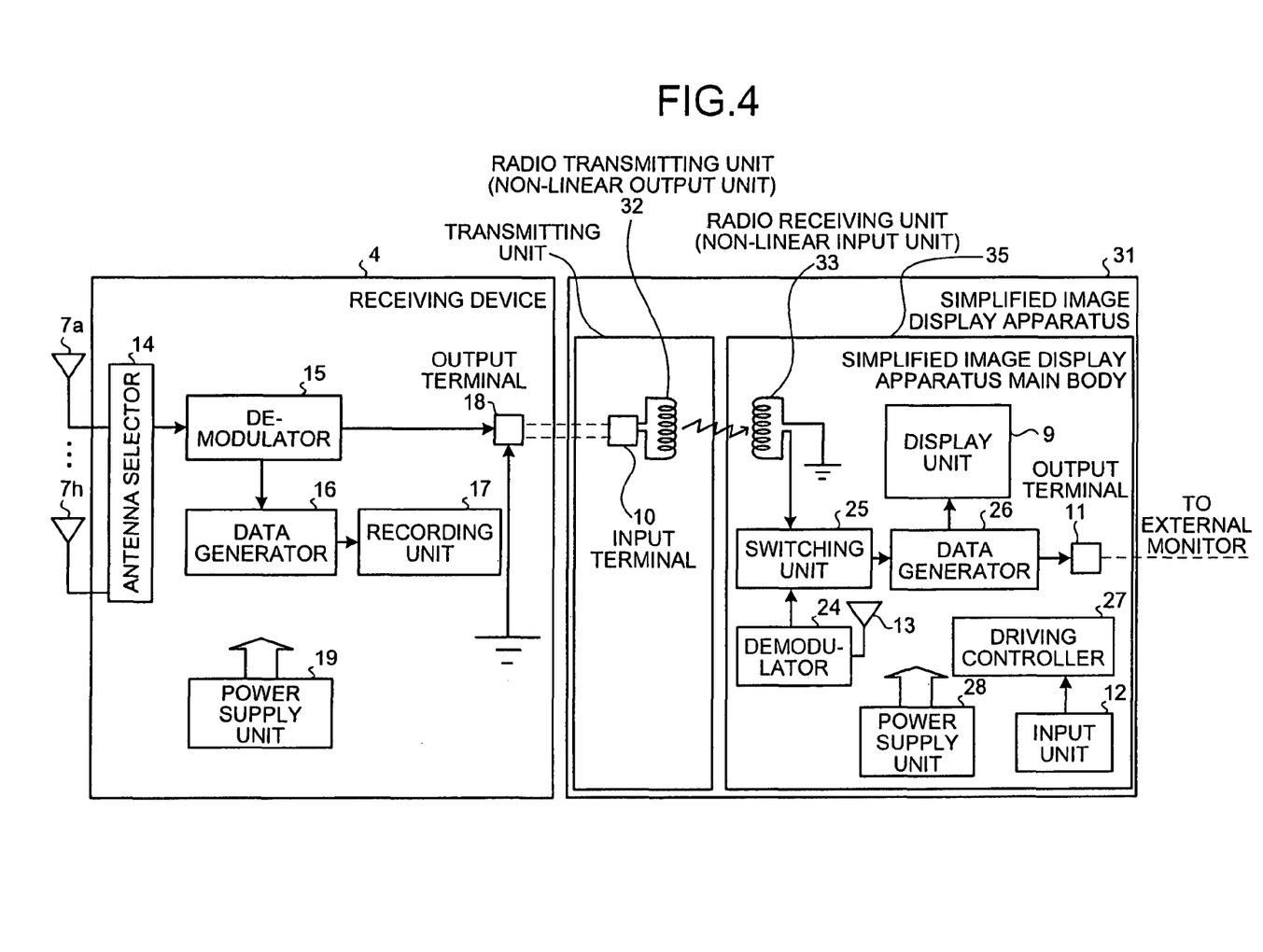
FIG. 4 is a schematic block diagram showing a configuration of a receiving system according to a second embodiment.

FIG. 4 is a schematic block diagram showing a configuration of the receiving system according to the second embodiment. As shown in FIG. 4, in the receiving system according to the second embodiment, the receiving system 4 has the same configuration as in the first embodiment. On the other hand, a simplified image display apparatus 31 has a configuration including a radio transmitting unit 32 and a radio receiving unit 33 instead of the light emitting unit 21 and the light receiving unit 22. In the second embodiment, as a configuration as seen from outside, the simplified image display apparatus 31 is formed of a transmitting unit 34 having built-in input terminal 10 and radio transmitting unit 32, and a simplified image display apparatus main body 35 formed separately from the transmitting unit 32 and having components other than the input terminal 10 and the radio transmitting unit 32 built therein. The transmitting unit 34 is used in a state of being mounted on the receiving device 4 at the time of use.

The radio transmitting unit 32 functions as an example of the non-linear output unit, and the radio receiving unit 33 functions as an example of the non-linear input unit. Specifically, the radio transmitting unit 32 and the radio receiving unit 33 have a function for transmitting the electric signal output from the radio receiving device 4 by the radio communications. That is, the radio transmitting unit 32 includes the transmitting circuit for converting the input electric signal to a radio signal and the transmitting antenna for transmitting the generated radio signal, and has a function for wirelessly transmitting the electric signal output from the receiving device 4. On the other hand, the radio receiving unit 33 includes a predetermined receiving antenna and a demodulation circuit, and has a function for performing receiving processing of the radio signal transmitted from the radio transmitting unit 32 to output the demodulated electric signal to the switching unit 25. It is desired that a frequency of the radio signal used for communications between the radio transmitting unit 32 and the radio receiving unit 33 have a value different from the frequency of the radio signal transmitted from the capsule endoscope 3 in order to avoid interference.

Thus, the signal can be transmitted between the non-linear output unit and the non-linear input unit by the radio communications. In other words, even when the configuration shown in FIG. 4 is adopted, the radio transmitting unit 32 as the non-linear output unit and the radio receiving unit 33 as the non-linear input unit are electrically insulated from each other, thereby preventing leakage current or the like from flowing from the external device 6 electrically connected to the radio receiving unit 33 to the receiving device 4 electrically connected to the radio transmitting unit 32.

In the second embodiment, the transmitting unit 34 can be used in such a state that the transmitting unit 34 is separated from the simplified image display apparatus main body 35 and mounted on the receiving device 4. When the transmitting unit 34 is used in the state of being mounted on the receiving device 4, there is an advantage in that a cable for electrically connecting it to the receiving device 4 is not required thereby facilitating the handling thereof. Further, even when the transmitting unit 34 is used in a state of being separated from the simplified image display apparatus main body 35, since the radio transmitting unit 32 can transmit the radio signal over a considerably wide range, there is no problem in reception by the radio receiving unit 33. Therefore, in the receiving system according to the second embodiment, the receiving device 4 (and the transmitting unit 34) and the simplified image display apparatus main body 35 can be handled as physically separate bodies without being connected by a cable or the like, thereby facilitating the handling.

Further, in the receiving system according to the second embodiment, the transmitting unit 34 is not built in the receiving device 4, but is configured so as to be detachable from the receiving device 4. By adopting such a configuration, when real-time viewing of the image is not performed, the receiving device 4 can perform the receiving processing in a state with the transmitting unit 34 being detached, thereby reducing the weight of the receiving device 4. Since the receiving device 4 is used in a state of being carried by the subject 2 at all times, by the weight reduction of the receiving device 4, burdens on the subject 2 can be reduced.

Third Embodiment

The receiving system according to a third embodiment is explained next. The simplified image display apparatus equipped in the receiving system according to the third embodiment has such a configuration that a transmission unit including the non-linear output unit and the non-linear input unit can be separated from the simplified image display apparatus main body, and the simplified image display apparatus can be electrically connected to the external monitor, only when the transmitting unit is mounted on the simplified image display apparatus main body.

Figure 5:
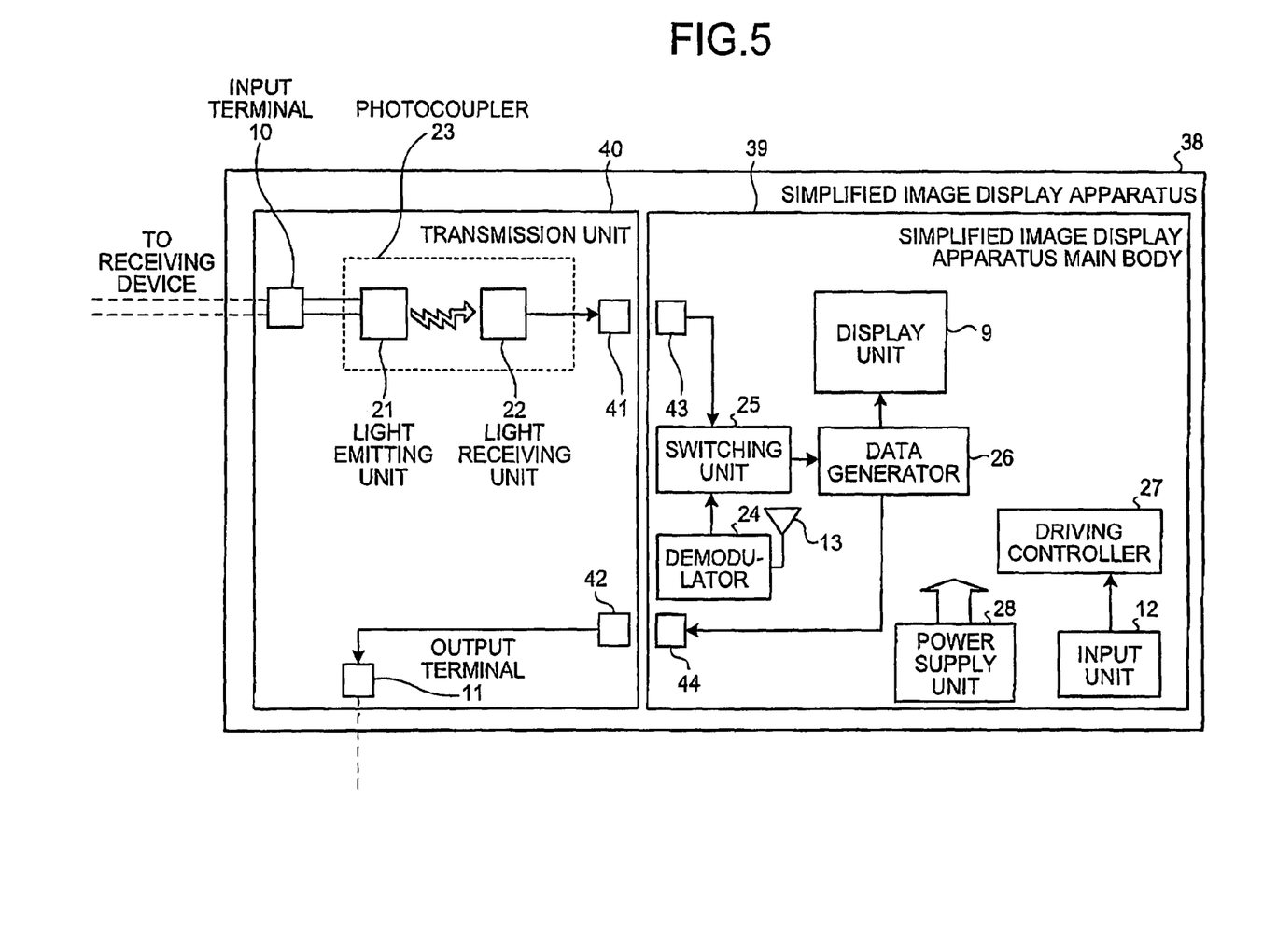
FIG. 5 is a schematic block diagram showing a configuration of a receiving system according to a third embodiment.

FIG. 5 is a schematic block diagram showing a configuration of a simplified image display apparatus 38 constituting the receiving system according to the third embodiment. In the third embodiment, since the configuration of the receiving device constituting the receiving system is the same as that of the first and second embodiments, and hence the illustration thereof is omitted.

As shown in FIG. 5, the simplified image display apparatus 38 according to the third embodiment is formed of a simplified image display apparatus main body 39 and a transmission unit 40, and the transmission unit 40 is formed detachable from the simplified image display apparatus main body 39. Configurations of the simplified image display apparatus main body 39 and the transmission unit 40 are explained below.

The transmission unit 40 includes the input terminal 10, the output terminal 11, and the photocoupler 23 therein, and also includes terminals 41 and 42 for electrically connecting to the simplified image display apparatus main body 39. Specifically, the terminal 41 is electrically connected to the light receiving unit 22 constituting the photocoupler 23, and is electrically connected to a terminal 43 (described later) equipped in the simplified image display apparatus main body 39 when the transmission unit 40 is mounted on the simplified image display apparatus main body 39. The terminal 42 functions as an example of a first terminal, and electrically connects to the output terminal 11. The terminal 42 is formed on the external surface of the transmission unit 40, and formed so as to electrically connect to a terminal 44 (described later) equipped in the simplified image display apparatus main body 39 when the transmission unit 40 is mounted on the simplified image display apparatus main body 39.

The simplified image display apparatus main body 39 includes the display unit 9, the input unit 12, the receiving antenna 13, the demodulator 24, the switching unit 25, the data generator 26, the driving controller 27, and the power supply unit 28, and newly includes the terminals 43 and 44. The terminal 43 is formed so as to electrically connect to the terminal 41 equipped in the transmission unit 40 when the transmission unit 40 is mounted on the simplified image display apparatus main body 39. The terminal 44 functions as an example of a second terminal, and formed at a position on the external surface of the simplified image display apparatus main body 39, electrically connected to the terminal 42 equipped in the transmission unit 40 when the transmission unit 40 is mounted on the simplified image display apparatus main body 39. The terminal 44 is formed so as to have a different shape from that of the output terminal 11, and hardly be directly connected to the cable or the like electrically connected to the external monitor 6.

An advantage of the receiving system according to the third embodiment is explained next. Since the simplified image display apparatus 38 according to the third embodiment has a configuration in which the output terminal 11 is arranged in the transmission unit 40, when only the simplified image display apparatus main body 39 is used, the simplified image display apparatus main body 39 cannot be electrically connected to the external monitor 6. In other words, the simplified image display apparatus 38 has a configuration capable of electrically connecting to the external monitor 6 only when the transmission unit 40 is mounted thereon.

Accordingly, in the receiving system according to the third embodiment, there is an advantage in that electrical connection between the receiving device 4 and the external monitor 6 not using the non-linear output unit (the light emitting unit 21) and the non-linear input unit (the light receiving unit 22) can be prevented. When user's knowledge is not sufficient, there is a possibility that the transmission unit 40 detached from the simplified image display apparatus main body 39 be connected to the receiving device 4. In this case, if the simplified image display apparatus main body 39 and the external monitor 6 can be electrically connected, the receiving device 4 and the external monitor 6 are electrically connected, which causes inflow of the leakage current generated by the external monitor 6 to the receiving device 4.

In the third embodiment, therefore, a configuration in which the output terminal 11 is also equipped in the transmission unit 40 is adopted. By adopting such a configuration, the simplified image display apparatus 38 cannot be physically connected to the external monitor 6, in a state with the transmission unit 40 being detached. Therefore, even when the user's knowledge is not sufficient at the time of using the receiving system according to the third embodiment, electrical connection between the receiving device 4 and the external monitor 6 can be prevented.

In the third embodiment, such a safety measure is taken, and the transmission unit 40 is made detachable from the simplified image display apparatus main body 39. By making the transmission unit 40 detachable, for example, the radio signal from the capsule endoscope 3 is received by the receiving antenna 13 equipped in the simplified image display apparatus main body 39 without using the receiving device 4, and at the time of viewing the image on the display unit 9, the light simplified image display apparatus 38, with the unnecessary transmission unit 40 being detached, can be used with low power consumption.

Fourth Embodiment

The receiving system according to a fourth embodiment is explained next. The receiving system according to the fourth embodiment has the same configuration as that of the third embodiment, wherein the transmitting unit can be separated from the body, and it newly includes a conduction controller that electrically determines presence of attachment of the transmission unit, and when the transmission is not attached, releases electrical connection to the external monitor.

Figure 6:
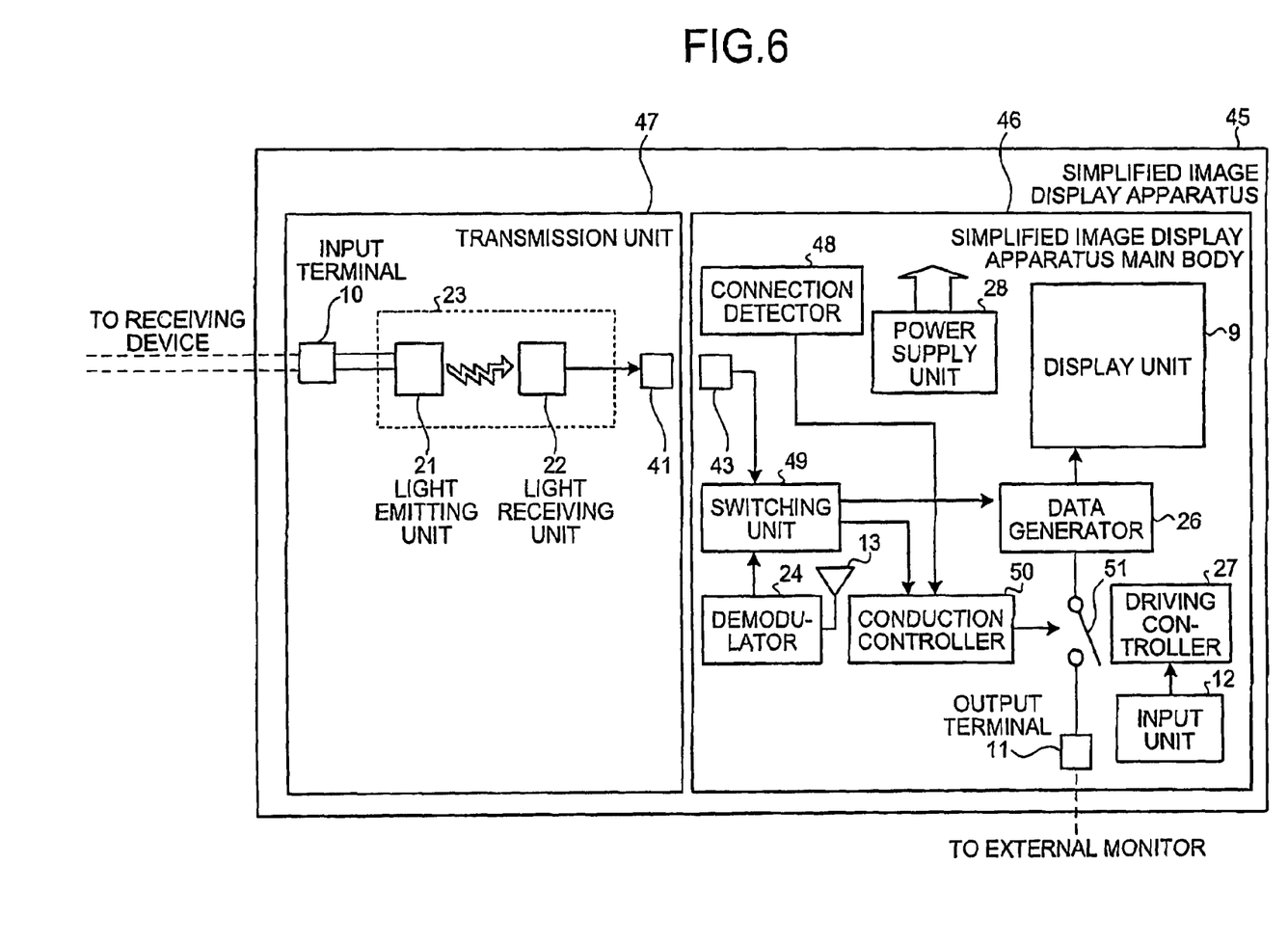
FIG. 6 is a schematic block diagram showing a configuration of a receiving system according to a fourth embodiment.

FIG. 6 is a schematic block diagram showing a configuration of the simplified image display apparatus constituting the receiving system according to the fourth embodiment. The receiving system according to the fourth embodiment includes the receiving device 4 having the same configuration as that of the first and the third embodiments, and hence the description of the receiving device 4 is omitted, like the third embodiment.

As shown in FIG. 6, a simplified image display apparatus 45 in the fourth embodiment is formed of a simplified image display apparatus main body 46 and a transmission unit 47 formed detachable from the simplified image display apparatus main body 46. The transmission unit 47 includes the input terminal 10, the photocoupler 23, and the terminal 41, as in the transmission unit 40 according to the third embodiment. However, it is different from the third embodiment in that it does not include the output terminal 11 and the terminal 42.

The simplified image display apparatus main body 46 includes the display unit 9, the input unit 12, the receiving antenna 13, the demodulator 24, the data generator 26, the power supply unit 28, and the terminal 43, as in the simplified image display apparatus main body 39 according to the third embodiment. On the other hand, the simplified image display apparatus main body 46 further includes the output terminal 11, a connection detector 48 that detects presence of electrical connection between the terminals 41 and 43, a switching unit 49 having a function for outputting information of a switching mode in addition to the function of the switching unit 25, and a conduction controller 50 that controls ON/OFF of a switching element 51 arranged between the data generator 26 and the output terminal 11, based on the information from the connection detector 48 and the switching unit 49.

The connection detector 48 detects the presence of electrical connection between the terminals 41 and 43, thereby outputting the detection result to the conduction controller 50.

The switching unit 49 has a function for outputting the information of the switching mode to the conduction controller 50, in addition to the function of the switching unit 25 according to the first to the third embodiments. Specifically, the switching unit 49 has a function for outputting switching information regarding to which of the electric signal input from the receiving device 4 or the electric signal input from the demodulator 24 the electric signal to be output is switched.

The conduction controller 50 has a function for controlling the electrical conduction of the output terminal 11 relative to the components such as the data generator 26 by controlling ON/OFF of the switching element 51 arranged between the data generator 26 and the output terminal 11. Specifically, the conduction controller 50 has a function for controlling ON/OFF of the switching element 51 based on the information input from the connection detector 48 and the switching unit 49.

Figure 7:
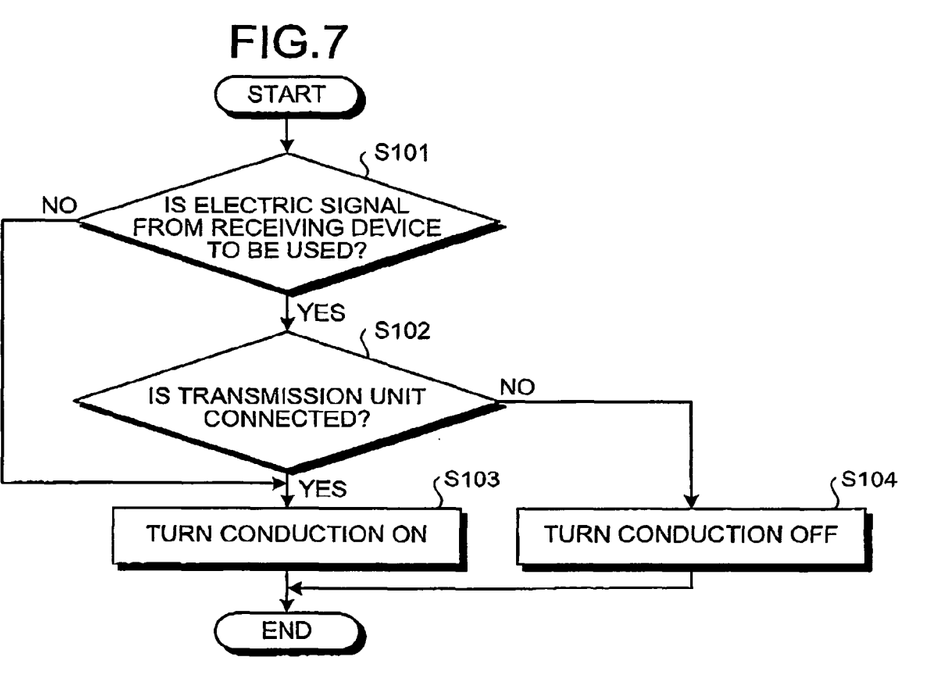
FIG. 7 is a flowchart for explaining an operation of a conduction controller equipped in the receiving system.

An operation of the conduction controller 50 is explained next. FIG. 7 is a flowchart for explaining an operation of the conduction controller 50 at the time of performing the conduction control. The conduction controller 50 determines whether the electric signal used for generating the image data is input from the receiving device 4 based on the information input from the switching unit 49 (step S101). When the electric signal output from the receiving device 4 is not used, but the electric signal output from the demodulator 24 is used (step S101, No), the control proceeds to step S103.

On the other hand, when it is determined to use the electric signal output from the receiving device 4 for generating the image data at step S101 (step S101, Yes), the conduction controller 50 determines whether the transmission unit 47 is mounted on the simplified image display apparatus main body 46 based on the information from the connection detector 48 (step S102). When it is determined that the transmission unit 47 is mounted (step S102, Yes), the conduction controller 50 controls so that the switching element 51 is turned on (step S103). On the other hand, when it is determined that the transmission unit 47 is not mounted (step S102, No), the conduction controller 50 controls so that the switching element 51 is turned off (step S104).

Inflow of the current from the external monitor 6 to the receiving device 4 can be prevented, and the external monitor 6 can be effectively used by performing the determination processing shown at steps S101 and 102. In other words, when the electric signal used for generating the image data in the simplified image display apparatus 45 is output from the demodulator 24, the switching unit 49 operates so as to electrically connect the demodulator 24 to the data generator 26, and insulate the data generator 26 from the terminal 43. Accordingly, in this case (step S101, No), the external monitor 6 and the receiving device 4 are not electrically connected to each other, regardless of the presence of the connection to the receiving device 4 via the photocoupler 23, and the switching element 51 need not be turned off. Accordingly, when the determination result at step S101 is No, the conduction controller 50 controls the switching element 51 to the ON state to output the generated image data to the external monitor 6, regardless of the transmission unit 47 being mounted.

On the other hand, when it is determined Yes at step S101, determination whether the transmission unit 47 is mounted becomes important. That is, when the transmission unit 47 is not mounted, since there is a possibility that the simplified image display apparatus main body 46 and the receiving device 4 can be electrically connected with each other, not using the transmission unit 47, there is a possibility that the receiving device 4 and the external monitor 6 can be electrically connected with each other via the simplified image display apparatus main body 46. Accordingly, when it is determined Yes at step S101, the conduction controller 50 determines whether the transmission unit 47 is mounted at step S102. When the transmission unit 47 is not mounted (step S102, No), the conduction controller 50 uniformly controls so that the switching element 51 is turned off (step S104). Since the switching element 51 is arranged between the output terminal 11 and the data generator 26, the output terminal 11 is insulated from the component such as the data generator 26 by turning off the switching element 51. Accordingly, it can be prevented that the external monitor 6 and the receiving device 4 are electrically connected with each other via the simplified image display apparatus main body 46, even when the transmission unit 47 is not mounted.

INDUSTRIAL APPLICABILITY

As described above, the simplified image display apparatus and the receiving system according to the present invention are useful for a simplified image display apparatus that can output image data to be displayed to a large external monitor, and particularly, suitable for a simplified image display apparatus connected to the receiving device for the capsule endoscope and used for viewing the image.

The invention claimed is:

1. A simplified image display apparatus capable of generating image data based on an electric signal generated by receiving processing of a receiving device, which is used in a state of being carried by a subject, displaying images based on the generated image data, and outputting the image data to an external device, comprising:
    a non-linear output unit electrically connected to the receiving device at the time of use, to output the electric signal input from the receiving device non-linearly to an output target not using a conducting wire;
    a non-linear input unit electrically insulated from the non-linear output unit, to input the electric signal output from the non-linear output unit;
    a display unit that displays image data based on the electric signal input by the non-linear input unit; and
    an output terminal electrically connected to the external device, to output the image data based on the electric signal input by the non-linear input unit to the external device,
    the non-linear output unit, the non-liner input unit, and the output terminal are formed in a transmission unit formed detachably relative to a simplified image display apparatus main body, and
    the output terminal is electrically connected to the non-linear input unit only when the transmission unit is attached to the simplified image display apparatus main body.

2. The simplified image display apparatus according to claim 1, wherein
    the non-linear output unit converts the electric signal input from the receiving device to an optical signal and outputs the optical signal, and
    the non-linear input unit receives the optical signal output from the non-linear output unit, and applies photoelectric conversion processing to the received optical signal, thereby reproducing the electric signal.

3. The simplified image display apparatus according to claim 2, wherein the non-linear output unit and the non-linear input unit form a photocoupler.

4. The simplified image display apparatus according to claim 1, wherein
    the non-linear output unit transmits a radio signal generated based on the electric signal, and
    the non-linear input unit receives the radio signal, and applies predetermined receiving processing to the radio signal, thereby reproducing the electric signal.

5. The simplified image display apparatus according to claim 1, wherein
    the output terminal is electrically connected to a first terminal arranged on a surface of the transmission unit and on a face brought into contact with the simplified image display apparatus main body at the time of attachment, and
    the non-linear input unit is electrically connected to a second terminal arranged on a surface of the simplified image display apparatus main body and at a position brought into contact with the first terminal at the time of attachment of the transmission unit.

6. The simplified image display apparatus according to claim 1, further comprising:
    an attachment detector that detects presence of attachment of a casing relative to the simplified image display apparatus main body; and
    a conduction controller that controls electrical conduction of the output terminal relative to other components based on a detection result of the attachment detector.

7. A receiving system including a receiving device carried by a subject to perform receiving processing of a radio signal transmitted from a body-insertable apparatus inserted into the subject, and a simplified image display apparatus capable of generating image data based on an electric signal acquired by receiving processing of the receiving device, displaying images based on the generated image data, and outputting the image data to an external device, wherein
    the receiving device includes
    a demodulator that performs demodulation of the radio signal received via a predetermined receiving antenna, and
    an output terminal that outputs at least an electric signal demodulated by the demodulator to the outside, and
    the simplified image display apparatus includes
    an input terminal electrically connected to the output terminal at the time of use to input the electric signal,
    a non-linear output unit that non-linearly outputs the electric signal input from the receiving device via the input terminal to an output target not using a conducting wire,
    a non-linear input unit electrically insulated from the non-linear output unit, to input the electric signal output from the non-linear output unit,
    a display unit that displays image data based on the electric signal input by the non-linear input unit, and
    an output terminal electrically connected to the external device, to output the image data based on the electric signal input by the non-linear input unit to the external device,
    the non-linear output unit, the non-liner input unit, and the output terminal are formed in a transmission unit formed detachably relative to a simplified image display apparatus main body, and
    the output terminal is electrically connected to the non-linear input unit only when the transmission unit is attached to the simplified image display apparatus main body.

* * * * *